United States Patent
Bogogna et al.

(10) Patent No.: US 9,567,308 B1
(45) Date of Patent: Feb. 14, 2017

(54) PROCESS FOR THE SYNTHESIS OF CHLORZOXAZONE

(71) Applicant: Procos S.P.A., Cameri (IT)

(72) Inventors: Luigi Bogogna, Cameri (IT); Lavinia Cicione, Novara (IT); Alessandro Barozza, Nosate (IT); Jacopo Roletto, Turin (IT); Paolo Paissoni, Druento (IT)

(73) Assignee: PROCOS S.P.A., Cameri (IT)

( * ) Notice: Subject to any disclaimer, the term of this patent is extended or adjusted under 35 U.S.C. 154(b) by 0 days.

(21) Appl. No.: 15/214,499

(22) Filed: Jul. 20, 2016

(30) Foreign Application Priority Data

Jul. 23, 2015 (IT) .................. 102015000037594

(51) Int. Cl.
*C07D 263/58* (2006.01)
(52) U.S. Cl.
CPC .................. *C07D 263/58* (2013.01)
(58) Field of Classification Search
None
See application file for complete search history.

(56) References Cited

U.S. PATENT DOCUMENTS

| | | |
|---|---|---|
| 2,895,877 A | 7/1959 | Marsh |
| 3,812,138 A | 5/1974 | Heise et al. |

FOREIGN PATENT DOCUMENTS

EP 0087347 A1 8/1983

OTHER PUBLICATIONS

Search Report and Written Opinion of ITUB20152422 of Nov. 23, 2015.
Singh, et al., "Synthesis of benzoxazole-2-ones, benzothiazole-2-ones and their 2-thione derivatives: efficient conversion of 2-thione to 2-oxo derivatives", Indian Journal of Chemistry, vol. 46B, 2007, pp. 1666-1671.

*Primary Examiner* — Kamal Saeed
(74) *Attorney, Agent, or Firm* — Silvia Salvadori, P.C.; Silvia Salvadori

(57) ABSTRACT

Disclosed is a process for the synthesis of chlorzoxazone (1) from 4-chloro-2-aminophenol and ethyl chloroformate in the presence of a base.

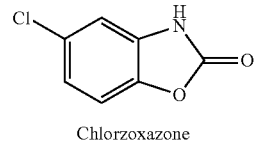

Chlorzoxazone

The process is particularly advantageous because it uses ethyl chloroformate instead of triphosgene, a highly dangerous reagent that releases phosgene and must be handled with extremely strict procedures to guarantee the safety of operators in industrial facilities.
Ethyl chloroformate allows the possibility of working with a number of solvents, including water.
The yield and purity of the product obtained are very high.

9 Claims, No Drawings

PROCESS FOR THE SYNTHESIS OF CHLORZOXAZONE

This Application claims priority to and the benefit of Italian Patent Application No. 102015000037594 filed on Jul. 23, 2015, incorporated herein by reference in its entirety.

BACKGROUND OF THE INVENTION

Chlorzoxazone, 5-chlorobenzo[d]oxazol-2(3H)-one, is a muscle relaxant which acts at central level and is used in the treatment of muscle spasms and the resulting pain. Chlorzoxazone acts on the spinal cord, by depressing/suppressing the reflexes.

A number of examples of synthesis of chlorzoxazone (1) from 4-chloro-2-aminophenol, into which an acyl group, usually from urea or phosgene, is inserted, are described in the literature. Cases in which the carbonyl group inserted is directly gaseous CO are also reported.

A representative example of the use of urea for the synthesis of chlorzoxazone (1) is reported in U.S. Pat. No. 3,812,138 (DE2131366), which discloses the formation of dibenzothiazolones from various aminophenols/aminothiols in the presence of urea and mineral acids according to the following synthesis scheme:

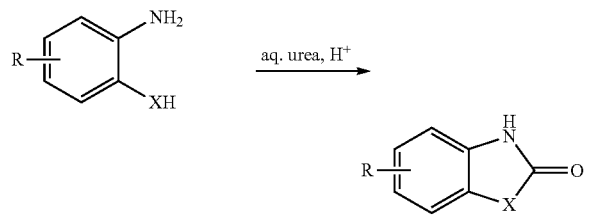

Specifically, chlorzoxazone (1) is synthesised by loading concentrated HCl, 4-chloro-2-aminophenol and urea into an autoclave and heating them in an inert atmosphere at 125° C. After cooling to room temperature, the crystalline paste that precipitates is suspended in 1500 parts of water, the pH of the suspension is adjusted to 5-6, and the paste is heated at 100° C. for an hour. After cooling, the residue is filtered and washed under vacuum to obtain chlorzoxazone (1) with a yield of 91%.

The patent does not report the degree of purity of the product obtained and, despite the high yield of the process, this synthesis is not particularly economical in terms of energy because very high temperatures are used. Moreover, the required work-up considerably increases the volumes of work, making it inefficient on an industrial scale.

CN1560040 and CN103360336 also report the synthesis of chlorzoxazone (1) by reacting 4-chloro-2-aminophenol with urea at high temperatures in the presence of mineral acids (HCl or $H_2SO_4$).

CN1560040 also discloses the synthesis of chlorzoxazone using phosgene

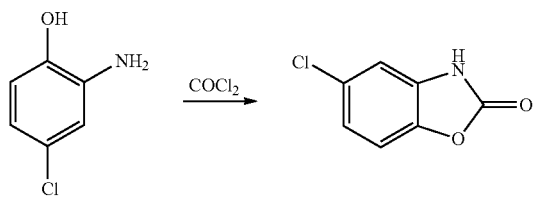

The same document also describes the synthesis of chlorzoxazone (1) from the nitro derivative by reacting it with gaseous CO, which leads to the formation of cyclic carbamate

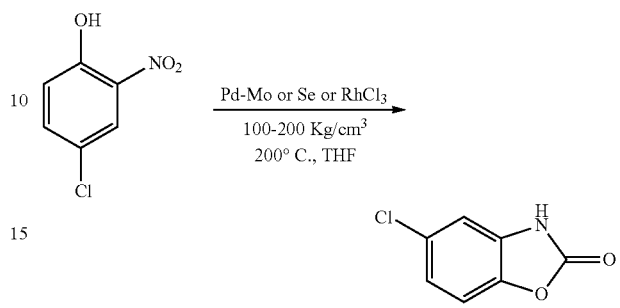

Another synthesis method involves cyclisation of 5-chloro-salicylamide by the action of 13% NaOH.

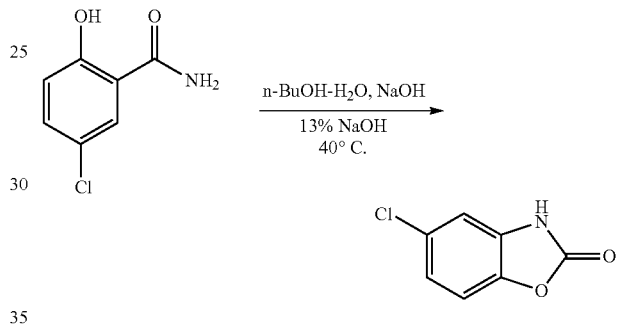

An alternative process using phosgene is reported in U.S. Pat. No. 3,369,022. The cyclisation of 4-chloro-2-aminophenol is described in procedure no. 2, according to the following synthesis scheme:

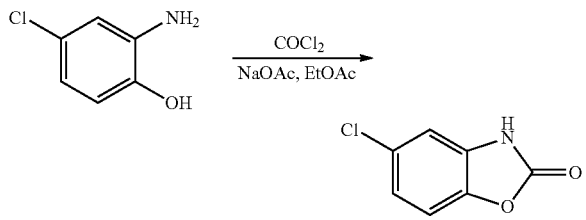

In particular, a solution of phosgene in ethyl acetate is dripped into a suspension of 4-chloro-2-aminophenol and sodium acetate in ethyl acetate. The reaction mixture is heated to reflux and cooled, then washed with water containing 5% hydrochloric acid. After a distillation under vacuum and a further crystallisation, the product is obtained.

The procedure does not provide any data relating to the yield or purity of the chlorzoxazone (1) obtained, but even if they were excellent, the process presents the significant drawback of the manageability of phosgene, a particularly reactive, toxic reagent which requires special precautions for both use and disposal.

Another example of synthesis of chlorzoxazone (1) involving the use of phosgene is reported in EP0477819. The procedure described therein also appears unsatisfactory in terms of yields.

Alternative methods of synthesising chlorzoxazone are described in U.S. Pat. No. 2,895,877. Starting with 2-amino-5-chlorobenzoxazole or N-(5-chloro-2-hydroxyphenyl)urea at reflux in 1N HCl a solid precipitates which, after a basic work-up and an acid work-up, is crystallised from a suitable solvent.

An alternative synthesis method not requiring the use of urea or phosgene is described in JP4834875, wherein a mixture of 4-chloro-2-nitrophenol, benzene, $RhCl_3$ and $V_2O_5$ is heated in an autoclave with CO.

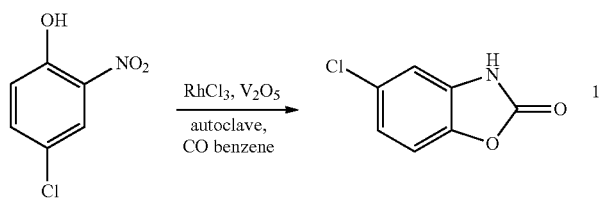

Also in JP58225072, chlorzoxazone (1) is obtained by heating a suitable nitrophenol with CO in hydrated organic solvent (e.g. THF) in the presence of a base (e.g. triethylamine) and selenium.

SK278412 describes a process wherein 4-chloro-2-nitrophenol is carbonylated with CO at high temperatures in the presence of catalytic systems such as S, COS, $H_2S$ or CS, bases (alkoxides, alkaline metal oxides, etc.) and vanadium derivatives ($V_2O_5$, $V_2S_5$, $NH_3VO_3$).

EP0087347 discloses (Example 7) the synthesis of chlorzoxazone (1) obtained directly from the nitro derivative in the presence of pyridine and of a catalyst based on palladium and molybdenum in a CO atmosphere (200 bars) at 200° C. Cyclic carbamate is then isolated by cooling, filtration of the catalyst and recrystallisation of the product from water.

The use of CO is problematic; said gas is highly poisonous, and insidious because it is odourless, colourless and tasteless. Its extremely hazardous nature requires particular precautions which make its industrial use extremely complicated.

RO75779 discloses the synthesis of chlorzoxazone (1) from 5-Cl-salicylamide; in particular, the desired product is obtained by treating the amide in water, NaOH and butanol with 13% NaOCl at 35° C.

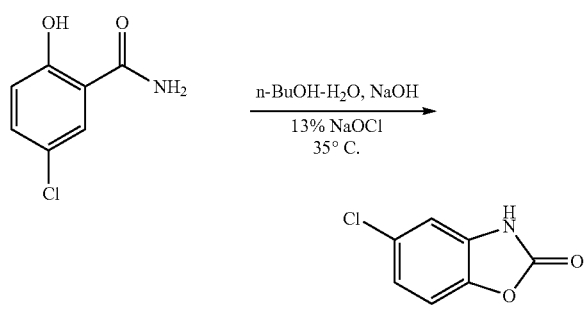

On the basis of the information set out above, there is clearly a need to find a process for synthesising chlorzoxazone (1) that is easier to manage industrially, safer, by avoiding the use of reagents which are extremely hazardous to humans and the environment, and more economical.

DESCRIPTION OF THE INVENTION

An advantageous process for the preparation of chlorzoxazone (1) has been found wherein 4-chloro-2-aminophenol is surprisingly closed with cyclic urethane due to ethyl chloroformate in the presence of a base, according to the following scheme:

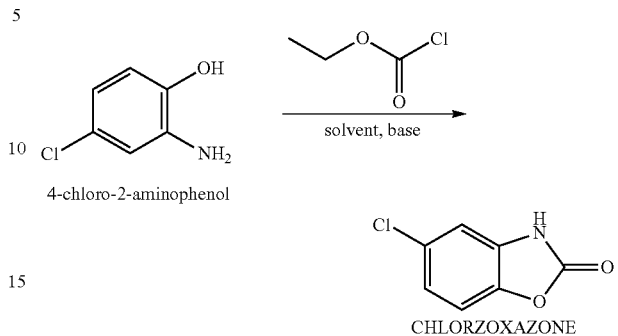

The process takes place by degrees, without isolation of intermediate reaction products.

The process therefore comprises:
1) acylation of 4-chloro-2-aminophenol (cyclisation of the various acylation products);
2) isolation of chlorzoxazone (1) from the reaction mixture by simple filtration of the reaction solvent.

The process of the invention typically involves the synthesis of chlorzoxazone (1) by acylation of 4-chloro-2-aminophenol with ethyl chloroformate in an organic solvent selected from acetonitrile, N,N-dimethylformamide, dichloromethane, toluene, acetone and ethyl acetate, or in water in the presence of an inorganic base, preferably potassium carbonate, potassium bicarbonate, sodium carbonate or sodium bicarbonate.

The order in which the various solvents, raw materials and base are added can differ from that reported below.

Chlorzoxazone (1) obtained is isolated directly from the reaction mixture by simple filtration. The quality of the synthesised product exceeds 98%.

According to a preferred embodiment of the invention, the process is performed as follows:

1 mole of 4-chloro-2-aminophenol is reacted with 0.9-1.5 moles of ethyl chloroformate, preferably 1.2-1.4 moles, in the presence of an inorganic base, preferably potassium carbonate, in quantities ranging from 1.0 to 4.0 moles, preferably from 2.0 to 3.0 mole equivalents. The reaction is performed in organic solvent or mixtures of solvents selected from acetonitrile, N,N-dimethylformamide, dichloromethane, toluene, acetone and ethyl acetate or in water, preferably in ethyl acetate, acetonitrile, N,N-dimethylformamide and water, in the temperature range between 0° C. (addition temperature) and 80° C. or reflux temperature in the case of low-boiling solvents, preferably at the temperature of 55-60° C. 4-15 volumes of solvent are used, preferably 5-7 volumes relative to the quantity of 4-chloro-2-aminophenol. The reaction is monitored by UPLC analysis using an ACQUITY UPLC® BEH C18 column, 17 μm, 2.1×50 mm, and water/acetonitrile/0.1% formic acid as eluent phase. After completion of the reaction, the reaction mixture containing chlorzoxazone (1) is cooled to the temperature of 0-25° C., preferably 0-10° C., and filtered. The solid is re-washed with water and dried under vacuum at the temperature of 30-90° C., preferably 60-70° C., to obtain chlorzoxazone with a purity exceeding 98%. The resulting solid can be further purified if necessary by recrystallisation from ethyl acetate, ethanol or other known solvents.

The process of the invention is particularly advantageous in that ethyl chloroformate is cheap and readily available, is not classified as a toxic gas, unlike phosgene and CO, does not need strict anhydrous conditions, which means that the reaction can take place in water, and does not need high reaction temperatures as with the use of urea.

Moreover, chlorzoxazone (1) is obtained directly from the reaction mixture by simple filtration of the suspension at the end of the reaction with very high yields and quality, thus considerably simplifying the work-up stages described in the literature.

The invention is illustrated in detail in the following examples.

Example 1

Ethyl chloroformate (9.8 g, 90.5 mmol) is dripped into a suspension of potassium carbonate (27.9 g, 201.8 mol) and 4-chloro-2-aminophenol (10.0 g, 69.6 mmol) in ethyl acetate (70 mL), heated to 60° C., in 4 hours. After completion of the reaction, the mixture is cooled at 5° C. for 1.5 hours, and the reaction mixture is filtered and re-washed with ethyl acetate (15 mL). The crude product is reduced to a pulp in water for 1.5 hours, filtered under vacuum and washed with water (10 mL); chlorzoxazone (1) (11.1 g), with a purity exceeding 98%, is obtained. Molar yield from 4-chloro-2-aminophenol to chlorzoxazone: 94%.

Example 2

Ethyl chloroformate (2.9 g, 26.3 mmol) is dripped into a solution of 4-chloro-2-aminophenol (3.0 g, 20.9 mmol) and triethylamine (2.7 g, 26.3 mmol) in acetonitrile (20.9 mL), cooled to 0° C. The mixture is left under stirring at 0° C. for one hour, and potassium carbonate (8.4 g, 60.8 mmol) is then added. The resulting mixture is left under stirring at 60° C. for 18 h. After completion of the reaction, the mixture is cooled at 5° C. for 1.5 hours, and the reaction mixture is filtered and re-washed with acetonitrile (5 mL). The crude product is reduced to a pulp in water for 1.5 hours, filtered under vacuum and washed with water (10 mL); chlorzoxazone (1), with a purity exceeding 96%, is obtained. Molar yield from 4-chloro-2-aminophenol to chlorzoxazone: 92%.

Example 3

Ethyl chloroformate (1.96 g, 18.1 mmol) is dripped into a suspension of sodium bicarbonate (5.8 g, 69.0 mmol) and 4-chloro-2-aminophenol (2.0 g, 13.9 mmol) in water (11 ml) at 0° C. The mixture is left to stand at room temperature for about half an hour, after which potassium carbonate is added and the reaction mixture is heated to 55-60° C. The reaction is finished after 2 hours. The reaction mixture is filtered and re-washed with water (10 mL) to obtain chlorzoxazone (1) (2.3 g, 13.6 mol) with a purity exceeding 95%. Molar yield from 4-chloro-2-aminophenol to chlorzoxazone: 98%.

UPLC-MS [M-H]$^-$=168 m/z $^1$H-NMR (in DMSO) (chemical shifts expressed in ppm relative to the TMS signal): 11.82 (1H, s), 7.31 (1H, d), 7.15 (1H, dd), 7.13-7.11 (1H, m). $^{13}$C-NMR: 154.7, 142.6, 132.2, 128.2, 121.9, 111.2, 110.3.

The invention claimed is:

1. A process for the preparation of chlorzoxazone (1) wherein 4-chloro-2-aminophenol is reacted with ethyl chloroformate in the presence of a solvent and a base, according to the following scheme:

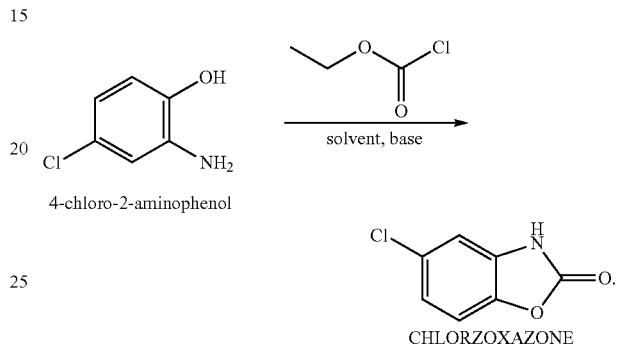

2. A process according to claim 1 wherein the solvent is selected from acetonitrile, N,N-dimethylformamide, dichloromethane, toluene, acetone, ethyl acetate or water.

3. A process according to claim 1 wherein the base is selected from potassium carbonate, potassium bicarbonate, sodium carbonate and sodium bicarbonate.

4. A process according to claim 1 wherein the molar ratio of 4-chloro-2-aminophenol to ethyl chloroformate ranges from 0.9 to 1.5.

5. A process according to claim 1 wherein the reaction is carried out at a temperature ranging from 0° C. to 80° C. or the reflux temperature in the case of low-boiling solvents.

6. A process according to claim 1, wherein the solvent is selected from ethyl acetate, acetonitrile, N,N-dimethylformamide or water.

7. A process according to claim 1, wherein the base is potassium carbonate.

8. A process according to claim 1, wherein the molar ratio of 4-chloro-2-aminophenol to ethyl chloroformate ranges from 1.2 to 1.4.

9. A process according to claim 1, wherein the reaction is carried out at a temperature of 55-60° C.

* * * * *